United States Patent
Lange et al.

[19]

[11] Patent Number: 5,908,413
[45] Date of Patent: Jun. 1, 1999

[54] RADIOPAQUE CATHETER AND METHOD OF MANUFACTURE THEREOF

[75] Inventors: Michael R. Lange, St. Paul; Henry J. Pepin, Loretto; Alan R. Dombrowski, Oakdale, all of Minn.

[73] Assignee: SciMed Life Systems, Inc., Maple Grove, Minn.

[21] Appl. No.: 08/943,450

[22] Filed: Oct. 3, 1997

[51] Int. Cl.$^6$ ............................................. A61M 25/098
[52] U.S. Cl. ............................................ 604/529; 604/523
[58] Field of Search ..................... 600/431, 433, 600/434, 435; 604/264, 280, 282, 529

[56] References Cited

U.S. PATENT DOCUMENTS

| | | |
|---|---|---|
| 2,857,915 | 10/1958 | Sheridan . |
| 3,070,132 | 12/1962 | Sheridan . |
| 3,485,234 | 12/1969 | Stevens . |
| 3,529,633 | 9/1970 | Vaillancourt . |
| 3,605,750 | 9/1971 | Sheridan et al. . |
| 3,608,555 | 9/1971 | Greyson . |
| 3,618,614 | 11/1971 | Flynn ...................... 128/348 |
| 3,888,249 | 6/1975 | Spence . |
| 3,962,153 | 6/1976 | Gore . |
| 4,027,659 | 6/1977 | Slingluff . |
| 4,277,432 | 7/1981 | Woinowski . |
| 4,282,876 | 8/1981 | Flynn . |
| 4,283,447 | 8/1981 | Flynn . |
| 4,318,402 | 3/1982 | Vaillancourt . |
| 4,321,226 | 3/1982 | Markling . |
| 4,402,684 | 9/1983 | Jessup . |
| 4,425,919 | 1/1984 | Alston, Jr. et al. . |
| 4,430,083 | 2/1984 | Ganz et al. . |
| 4,469,483 | 9/1984 | Becker et al. . |
| 4,516,970 | 5/1985 | Kaufman et al. . |
| 4,516,972 | 5/1985 | Samson . |
| 4,563,181 | 1/1986 | Wijayarathna et al. . |
| 4,568,338 | 2/1986 | Todd . |
| 4,577,543 | 3/1986 | Wilson . |
| 4,588,399 | 5/1986 | Nebergall et al. . |
| 4,596,563 | 6/1986 | Pande . |
| 4,636,346 | 1/1987 | Gold et al. . |
| 4,657,024 | 4/1987 | Coneys . |
| 4,661,094 | 4/1987 | Simpson . |
| 4,665,604 | 5/1987 | Dubowik . |
| 4,690,175 | 9/1987 | Ouchi et al. . |
| 4,735,620 | 4/1988 | Ruiz . |
| 4,739,768 | 4/1988 | Engelson . |

(List continued on next page.)

OTHER PUBLICATIONS

Johnson, "Paste Extrusion of Filled TFE–Fluorocarbon Resin for Wire Insulations", *SPE Journal*, Feb., 1961, pp. 151–154.

"Tetrafluoroethylene Polymers", *Encyclopedia of Polymer Science and Technology*, vol. 13, Copyright 1970, John Wiley & Sons, Inc., pp. 623–654.

Carlson et al., *Fluoropolymers, Organic*, vol. AII, Copyright 1988, Verlagsgesellschaft mbH, Weinheim, Germany, pp. 393–428.

Lonz et al., "Extrusion Properties of Lubricated Resin from Coagulated Dispersion", *Industrial and Engineering Chemistry*, vol. 44, No. 8, Aug. 1952, pp. 1805–1810.

*Primary Examiner*—Wynn Wood Coggins
*Assistant Examiner*—LoAn H. Thanh
*Attorney, Agent, or Firm*—Crompton, Seager & Tufte LLC.

[57] ABSTRACT

Radiopaque catheter and method of manufacture thereof having a first layer and a second layer in a coaxial arrangement wherein each of the layers has a radiopaque filler material intermixed therewith. The radiopaque filler materials and/or the concentrations thereof may be the same or different for each of the layers. Further, the plastic binder material used for each of the layers may be the same or different. By selecting a high concentration of a highly radiopaque filler material for an inner layer and a lower concentration of a radiopaque filler that is selected to provide a relatively smooth surface, the X-ray visibility of the catheter may be maximized while still maintaining a relative smooth outer surface.

27 Claims, 2 Drawing Sheets

U.S. PATENT DOCUMENTS

| | | |
|---|---|---|
| 4,764,324 | 8/1988 | Burnham . |
| 4,784,638 | 11/1988 | Ghajar et al. . |
| 4,806,182 | 2/1989 | Rydell et al. . |
| 4,817,613 | 4/1989 | Jaraczewski et al. . |
| 4,838,879 | 6/1989 | Tanabe et al. . |
| 4,842,590 | 6/1989 | Tanabe et al. . |
| 4,863,442 | 9/1989 | DeMello et al. . |
| 4,886,506 | 12/1989 | Lovgren et al. ......................... 604/280 |
| 4,898,591 | 2/1990 | Jang et al. . |
| 4,925,710 | 5/1990 | Buck et al. . |
| 4,961,731 | 10/1990 | Bodicky et al. . |
| 4,963,306 | 10/1990 | Weldon . |
| 4,968,307 | 11/1990 | Dake et al. . |
| 5,019,057 | 5/1991 | Truckai . |
| 5,021,044 | 6/1991 | Sharkawy . |
| 5,037,403 | 8/1991 | Garcia . |
| 5,045,072 | 9/1991 | Castillo et al. ......................... 604/280 |
| 5,057,092 | 10/1991 | Webster, Jr. . |
| 5,061,257 | 10/1991 | Martinez et al. . |
| 5,069,673 | 12/1991 | Shwab . |
| 5,078,702 | 1/1992 | Pomeranz . |
| 5,088,991 | 2/1992 | Weldon . |
| 5,160,559 | 11/1992 | Scovil et al. . |
| 5,171,232 | 12/1992 | Castillo et al. ......................... 604/280 |
| 5,199,950 | 4/1993 | Schmitt et al. . |
| 5,201,723 | 4/1993 | Quinn . |
| 5,221,270 | 6/1993 | Parker ..................................... 604/282 |
| 5,234,416 | 8/1993 | Macaulay et al. ...................... 604/282 |
| 5,254,107 | 10/1993 | Soltesz ................................... 604/282 |
| 5,256,158 | 10/1993 | Tolkoff et al. ......................... 604/280 |
| 5,279,596 | 1/1994 | Castaneda et al. ..................... 604/282 |
| 5,300,048 | 4/1994 | Drewes, Jr. et al. ................... 604/280 |
| 5,306,263 | 4/1994 | Voda ...................................... 604/281 |
| 5,318,032 | 6/1994 | Lonsbury et al. ...................... 128/658 |
| 5,335,410 | 8/1994 | Brunham ................................ 29/452 |
| 5,358,493 | 10/1994 | Schweich, Jr. et al. ................ 604/264 |
| 5,389,090 | 2/1995 | Fischell et al. ......................... 604/280 |
| 5,399,164 | 3/1995 | Snoke et al. .............................. 604/95 |
| 5,401,258 | 3/1995 | Voda ...................................... 604/281 |
| 5,403,292 | 4/1995 | Ju ........................................... 604/282 |
| 5,425,723 | 6/1995 | Wang ..................................... 604/280 |
| 5,433,713 | 7/1995 | Trotta .................................... 604/264 |
| 5,441,489 | 8/1995 | Utsumi et al. ......................... 604/280 |
| 5,445,624 | 8/1995 | Jimenez ................................. 604/280 |
| 5,472,435 | 12/1995 | Sutton .................................... 604/282 |
| 5,489,277 | 2/1996 | Tolkoff et al. ......................... 604/280 |
| 5,509,910 | 4/1996 | Lunn ...................................... 604/282 |
| 5,514,236 | 5/1996 | Avellanet et al. ...................... 156/154 |
| 5,531,721 | 7/1996 | Pepin et al. ............................ 604/282 |
| 5,533,985 | 7/1996 | Wang ..................................... 604/246 |
| 5,538,512 | 7/1996 | Zenzon et al. ......................... 604/280 |
| 5,538,513 | 7/1996 | Okajima ................................ 604/282 |
| 5,542,924 | 8/1996 | Snoke et al. .............................. 604/95 |
| 5,542,937 | 8/1996 | Chee et al. ............................. 604/280 |
| 5,545,149 | 8/1996 | Brin et al. .............................. 604/265 |
| 5,545,151 | 8/1996 | O'Connor et al. ..................... 604/282 |
| 5,554,139 | 9/1996 | Okajima ................................ 604/282 |
| 5,569,200 | 10/1996 | Umeno et al. ............................ 604/96 |
| 5,569,218 | 10/1996 | Berg ...................................... 604/282 |
| 5,584,821 | 12/1996 | Hobbs et al. .......................... 604/280 |
| 5,599,319 | 2/1997 | Stevens .................................. 604/264 |
| 5,599,325 | 2/1997 | Ju et al. ................................. 604/282 |
| 5,599,326 | 2/1997 | Carter . |
| 5,603,705 | 2/1997 | Berg . |
| 5,614,136 | 3/1997 | Pepin et al. . |
| 5,658,263 | 8/1997 | Dang et al. . |
| 5,662,621 | 9/1997 | Lafontaine . |
| 5,662,622 | 9/1997 | Gore et al. . |
| 5,674,208 | 10/1997 | Berg et al. . |
| 5,676,659 | 10/1997 | McGurk . |
| 5,680,873 | 10/1997 | Berg et al. . |
| 5,695,483 | 12/1997 | Samson . |
| 5,702,373 | 12/1997 | Samson .................................. 604/282 |
| 5,779,731 | 7/1998 | Leavitt .................................. 604/194 |
| 5,814,016 | 9/1998 | Valley et al. ............................. 604/96 |
| 5,861,021 | 1/1999 | Thome et al. ......................... 607/101 |

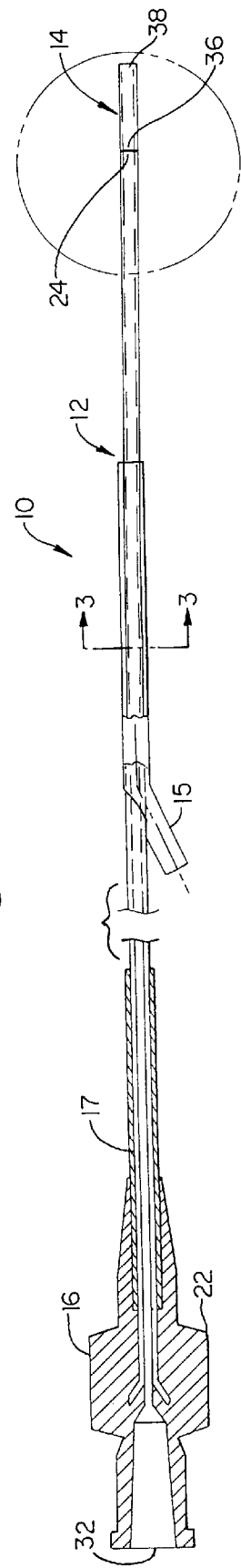
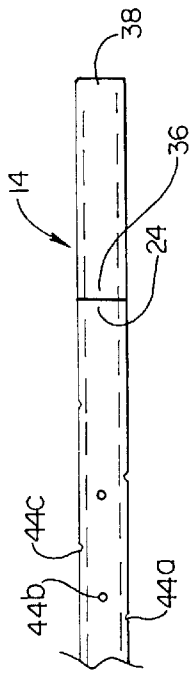
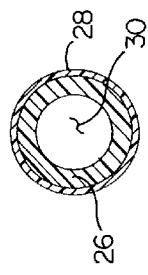
Fig. 1
Fig. 2
Fig. 3

RADIOPAQUE CATHETER AND METHOD OF MANUFACTURE THEREOF

TECHNICAL FIELD

This invention relates to the field of intravascular medical devices, and more particularly to the field of catheters such as angiographic and guide catheters used for the placement of medicines and medical devices within the body. More specifically, the invention relates to an improved catheter having increased radiographic visibility while optimizing the performance and surface characteristics of the same.

BACKGROUND OF THE INVENTION

Angiographic and guide catheters are well known in the field of medicine for use in conjunction with other catheters for the treatment of cardiovascular disease through such procedures as percutaneous transluminal coronary angioplasty (PTCA) procedures. Guide catheters aid in treatment of arterial lesions by providing a conduit for positioning dilatation balloon systems across an arterial stenosis. Angiographic catheters aid in delivering radiopaque dyes and the like into selected blood vessels to allow angiographic examination and the like of the blood vessels. The need for a greater variety of catheters to treat different types of circumstances has grown tremendously as the techniques for the use of such devices has grown.

During the treatment of cardiovascular disease, guide catheters and diagnostic catheters must be able to traverse tortuous pathways through blood vessels in a manner that minimizes trauma. In order for the physician to place the catheter at the correct location in the vessel, the physician must apply longitudinal and rotational forces thereto. Catheters must typically be stiff enough to transmit the required forces, while at the same time flexible enough to maneuver through the vascular system. For optimum performance and control, a catheter must achieve a balance between these often competing factors.

In many applications the catheter is guided through the aorta, over the aortic arch, and down to the ostium of the vessel which is to be treated or diagnosed. To reach such sites, the proximal section of the catheter is typically relatively rigid for transmitting the forces applied, and the distal section is more flexible to allow for better tracking and placement of the catheter within the vessels. One approach to increase the strength of the proximal section is to include a metal braid or coil therein. Another approach is to merely use a stiffer polymer in the proximal portion than in the distal portion.

In many surgical procedures, it is important to determine the location or position of the catheter within the body. This is often accomplished by incorporating a radiopaque material in the catheter. X-ray observation techniques can then be used to view the position of the catheter within the body.

It is known to mix a radiopaque material, typically in a powder or granular form with the plastic material of the catheter. One potential limitation of this approach is that the inner and outer surfaces of the catheter may become rough or course. This may be particularly problematic when the concentration of the radiopaque filler material is high, especially near the surface. For some radiopaque filler materials, high concentrations may be required to achieve the desired X-ray visibility. Another limitation may be that the radiopaque filler material may cause the plastic binder materials to lose their original and desired thermoplastic properties. Hard granular radiopaque materials in particular may detract from the desired flexibility ductility and maneuverability of the resulting tubing in direct proportion to the amount of radiopacity that they impart.

One approach for overcoming some of these limitations is disclosed in U.S. Pat. No. 4,657,024 of Coneys. Coneys suggests completely embedding and surrounding a radiopaque layer with a non-radiopaque plastic material. Presumably, since the plastic material that surrounds the radiopaque layer does not include any radiopaque filler materials the inner and outer surfaces of the medical-surgical tube can be made smooth.

Another approach is disclosed in U.S. Pat. No. 3,618,614 of Flynn. Flynn suggests providing one layer that is transparent to X-rays adjacent to another layer that is radiopaque. Flynn also suggests adding at least one material having plasticising properties or, in the alternative, providing a polymeric material which imparts greater flexibility and softness to the plastic material of the radiopaque layer so that the plastic material of the blend retains its desired properties of plasticity, softness and flexibility.

In both Coneys and Flynn, at least one layer is free from radiopaque filler material. Since it is often desirable to minimize the wall thickness of many catheters and maximize the radiopacity thereof, it would be beneficial to provide a multi-layer catheter tubing that includes at least some radiopaque material in at least two of the layers thereof. This may increase the X-ray visibility of the resulting catheter within the body.

SUMMARY OF THE INVENTION

The present invention overcomes many of the disadvantages found in the prior art by providing a catheter that includes a first layer and a second layer, in a coaxial arrangement, wherein each of the layers has a radiopaque filler material intermixed therewith. The radiopaque filler materials and/or concentrations may be the same or different for each of the layers. In addition, the plastic binder material used for each of the layers may be the same or different.

In an illustrative embodiment, a first tubular member is provided having a proximal end, a distal end, and a lumen extending therethrough. The first tubular member preferably includes a first radiopaque filler material intermixed with a first plastic material. A second tubular member, in coaxial relation with the first tubular member, is also provided and preferably includes a second radiopaque filler material intermixed with a second plastic material. The first radiopaque filler material is preferably different from the second radiopaque filler material. Further, the concentration of the first radiopaque filler material is preferably different than the concentration of the second radiopaque filler material.

The second tubular member may axially overlay the outer surface of the first tubular member. In this arrangement, the radiopaque filler material for the first tubular member may be selected to be highly radiopaque, and the radiopaque filler material for the second tubular member may be selected to provide a relatively smooth outer surface. Accordingly, the X-ray visibility of the catheter may be maximized, while still allowing a relatively smooth outer surface.

To further enhance the surface qualities of the second tubular member, the concentration of the radiopaque filler in the second tubular member may be less than the concentration of the radiopaque filler in the first tubular member. This may allow the first tubular member to have a relatively high concentration of radiopaque filler material for maximum radiopacity. Since the second tubular member may have a lower concentration of radiopaque filler material, and may use a radiopaque filler material that is selected to provide a relatively smooth surface, the surface of the second tubular member may remain relatively smooth.

The plastic materials used in the first and second tubular members may be selected to optimize the performance of the catheter. For example, the plastic material of the first tubular member may be different from the plastic material of the second tubular member. In a preferred embodiment, the plastic material used for the first and second tubular members is the same.

A distal tip may be attached to the distal end of the first and/or second tubular members. This may be accomplished by adhesive bonding, heat bonding, or any other attachment means. Moreover, it is contemplated that the distal tip may be integrally formed with the proximal shaft portion.

The distal tip may include yet another radiopaque filler material intermixed with yet another plastic material. In a preferred embodiment, the plastic material of the distal tip is the same material as used for the first and second tubular members, but has a lower durometer rating. Further, the radiopaque filler material of the distal tip is preferably the same type as that used in the first plastic tubular member, rendering the distal tip highly radiopaque. It is recognized, however, that the plastic material and/or radiopaque filler material may the same or different from that used in the first or second tubular members.

In addition to the above advantages, the addition of the outer tubular member, which is preferably filled with a non-metallic filler material such as bismuth subcarbonate, allows the outer surface of the proximal shaft to be colored. Most metallic filler materials, including a tungsten filler material, cause the mixture that contains the filler material to assume a particular color, such as black. Adding pigment or other colorant typically does not change the color of the mixture that has the metallic filler material therein.

Color can play an important role in the identification and use of selected catheters. Thus, by axially disposing an outer layer that includes a non-metallic filler material around an inner layer that includes a highly radiopaque metallic filler material, the resulting catheter may be both highly radiopaque and have the advantage of a colored outer surface.

Finally, a number of methods for forming a multi-layer tubular assembly for use in a catheter is contemplated. A first illustrative method includes the steps of: intermixing a first radiopaque filler material with a first plastic material, thereby providing a first extrudable material; intermixing a second radiopaque filler material with a second plastic material wherein the first radiopaque filler material is different from said second radiopaque filler material, thereby providing a second extrudable material; and co-extruding the first extrudable material and the second extrudable material to form the multi-layer tubular assembly. As discussed above, it is contemplated that the first plastic material may be the same or different from the second plastic material.

A second illustrative method comprises the steps of: intermixing a first radiopaque filler material with a first plastic material in a first concentration, thereby providing a first extrudable material; intermixing a second radiopaque filler material with a second plastic material in a second concentration, wherein the first concentration is different from the second concentration, thereby providing a second extrudable material; and co-extruding the first extrudable material and the second extrudable material to form the multi-layer tubular assembly.

A third illustrative method of the present invention comprises the steps of: intermixing a first radiopaque filler material with a first plastic material, thereby providing a first extrudable material; intermixing a second radiopaque filler material with a second plastic material wherein the first radiopaque filler material is different from said second radiopaque filler material, thereby providing a second extrudable material; extruding the first extrudable material; and extruding the second extrudable material in coaxial relation with the first extrudable material to form the multi-layer tubular assembly.

Finally, a fourth illustrative method of the present invention comprises the step of: intermixing a first radiopaque filler material with a first plastic material in a first concentration, thereby providing a first extrudable material; intermixing a second radiopaque filler material with a second plastic material in a second concentration, wherein the first concentration is different from the second concentration, thereby providing a second extrudable material; extruding the first extrudable material; and extruding the second extrudable material in coaxial relation with the first extrudable material to form the multi-layer tubular assembly.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a plan view with the hub in cross section of a catheter showing a preferred embodiment of the present invention;

FIG. 2 is a plan view showing a distal portion of the catheter of FIG. 1;

FIG. 3 is a cross section view of the catheter of FIG. 1 taken along line 3—3, with the straightener member omitted for clarity;

DETAILED DESCRIPTION OF THE PREFERRED EMBODIMENTS

Figure 4:
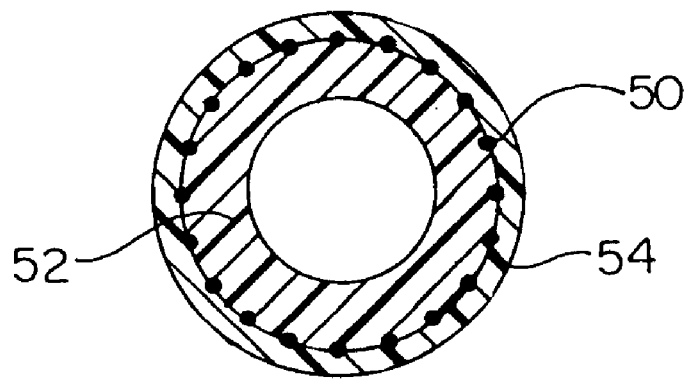
FIG. 4 is an alterative cross section of the catheter of FIG. 1 taken along line 3—3 showing a braid.

Referring now to the drawings, wherein like reference numerals refer to like elements throughout the several views, FIG. 1 is a plan view with the hub in cross section of a catheter showing a preferred embodiment of the present invention. FIG. 1 shows a catheter 10 which includes a proximal shaft portion 12, a distal tip portion 14, and a hub 16. Proximal shaft portion 12 has a proximal end 22 and a distal end 24. Proximal shaft portion 12 also includes an inner tubular member 26 and an outer tubular member 28 (see, FIG. 3). The inner tubular member 26 has a lumen 30 extending from proximal end 22 to distal end 24. Access to the lumen 30 is provided via proximal end 32 of hub 16.

A strain relief 17 is insert molded with hub 16. The proximal shaft portion 12 extends into hub 16 through strain relief 17. Strain relief 17 is preferably made from polyether block amide copolymer (PEBA) with titanium dioxide having a durometer of about 63 D, and colored white. PEBA is commercially available under the trademark PEBAX.

The proximal shaft portion 12 is preferably formed from two co-extruded layers of PEBA. It is recognized that two single extrusions may also be used. The inner tubular member 26 is preferably formed from PEBA having a durometer of 72 D, and is 70% loaded by weight with a tungsten filler. The outer tubular member 28 is preferably formed from PEBA having a durometer of 72 D, and is 30% loaded by weight with a bismuth subcarbonate filler. Both the inner tubular member 26 and the outer tubular member 28 also preferably include less than 1% by weight of a UV stabilizer.

The proximal shaft portion 12 defines the majority of the central lumen. The distal tip portion 14 defines the remainder of the central lumen, and is preferably formed from a single layer of PEBA having a durometer of 60 D, and is 65% loaded with a Tungsten filler. A less than 1% UV stabilizer is also provided. The distal tip 14 is aligned with the distal portion 24 of the proximal shaft portion 12, and is attached thereto in an abutting relation using a heat bonding process to form smooth inner and outer surfaces over the joint. The distal tip 14 is preferably approximately 1.5 inches long.

A tubular straightener member 15 is shown disposed around the proximal shaft portion 12. The straightener member 15 may facilitate the introduction of the catheter 10 into the body, particular when the distal tip 14 is provided with a preformed curve such as pigtail. Before insertion of the catheter 10, the straightener member 15 is typically slid distally until the distal tip 14 is disposed therein. The straightener member 15 is much more rigid than the distal tip 14, and thus tends to "straighten" the distal tip 14. This allows the distal tip 14 to be more easily inserted into a blood vessel.

Once the distal tip 14 is successfully inserted, the straightener member 15 is typically slid proximally as the catheter 10 is moved distally into the vessel. The straightener member preferably has a slit extending the full length thereof which allows the straightener member 15 to be removed from the shaft of catheter 10 in a peel away fashion and discarded.

FIG. 2 is a plan view showing the distal portion of catheter 10. Distal tip portion 14 has a proximal end 36, a distal end 38 and a lumen extending from proximal end 36 to distal end 38. Distal tip portion 14 is attached at proximal end 36 to distal end 24 of proximal shaft portion 12 such that the inner lumen 30 of proximal shaft portion 12 and the inner lumen of distal tip portion 14 form a continuous lumen extending from proximal end 22 of proximal shaft portion 12 to distal end 38 of distal tip portion 14. In a preferred embodiment, distal tip 14 is tapered so that the inner diameter is smaller to fit snugly over a guide wire.

Eight side holes are provided near the distal end 24 of the proximal shaft portion 12. Preferably, each of the side holes, for example side holes 44a–c, are spaced 2 mm apart and are 90° offset from adjacent side holes. Thus, the eight side holes are spaced in a helix pattern around the circumference of the distal end 24 of the proximal shaft portion 12. Each of the eight side holes is generally circular, and extend through the wall of the proximal shaft portion 12 along an axis that intersects, and is perpendicular to, the axis defined by the central lumen.

FIG. 3 is a cross-sectional view of FIG. 1 taken along line 3—3, with the straightener member 15 omitted for clarity. FIG. 3 specifically shows inner tubular member 26 and outer tubular member 28. Inner tubular member 26 includes a first radiopaque filler material intermixed with a first plastic material. Outer tubular member 28 includes a second radiopaque filler material intermixed with a second plastic material.

The radiopaque filler material of the inner tubular member 26 is preferably different from the radiopaque filler material of the outer tubular member 28. Further, the concentration of the radiopaque filler material of the inner tubular member 26 is preferably different than the concentration of the radiopaque filler material of the outer tubular member 28.

In a preferred embodiment, the radiopaque filler material for the inner tubular member 26 is selected to be highly radiopaque. Typically, metal based radiopaque fillers such as tungsten are preferred. The radiopaque filler material for the outer tubular member is selected to provide a relatively smooth outer surface, and preferably is a salt based radiopaque filler such as bismuth subcarbonate. In this arrangement, the X-ray visibility of the catheter 10 may be maximized, while still maintaining a relatively smooth outer surface.

To further enhance the surface qualities of the outer tubular member 28, the concentration of the radiopaque filler in the outer tubular member 28 may be less than the concentration of the radiopaque filler in the inner tubular member 26. As indicated above, the outer tubular member 28 is preferably 30% loaded by weight with a bismuth subcarbonate filler, while the inner tubular member 26 is preferably 70% loaded by weight with a tungsten filler. This may allow the inner tubular member 26 to have a relatively high concentration of radiopaque filler material for maximum radiopacity. At the same time, the outer tubular member 28 may have a lower concentration of radiopaque filler material, and may use a radiopaque filler material that is selected to provide a relatively smooth surface.

The plastic materials used in the inner and outer tubular members may be selected to optimize the performance of the catheter. In one embodiment, the plastic material of the inner tubular member 26 may be different from the plastic material of the outer tubular member 28. In a preferred embodiment, the plastic material used for the inner and outer tubular members is the same, namely, PEBA having a durometer of 72 D.

The distal tip portion 14 may include yet another radiopaque filler material intermixed with yet another plastic material. In a preferred embodiment, the plastic material of the distal tip is the same material as used for the inner and outer tubular members, but has a lower durometer rating (e.g. more flexible). The distal tip portion 14 is formed from PEBA having a durometer of 60 D. Further, the radiopaque filler material of the distal tip is preferably the same type as used in the inner tubular member 26, namely tungsten. This may render the distal tip highly radiopaque. Finally, the concentration of the radiopaque filler material in the distal tip portion 14 is preferably 65%, which is slightly lower than that of the inner tubular member 26, and less than 1% by weight of a UV stabilizer is added. It is recognized, however, that the plastic material and/or radiopaque filler material used in the distal tip 14 may the same or different from that used in the first or second tubular members.

Most metallic filler materials, including a tungsten filler material, cause the mixture that contains the filler material to assume a particular color. For example, the tungsten filler material that is preferably used in the inner tubular member 26 and the distal tip 14 typically causes these components to assume a black color. Adding pigment or other colorant typically does not change the color of the mixture that has the metallic filler material therein.

In addition to the above advantages, the addition of outer tubular member 28, which is preferably filled with a non-metallic filler material such as bismuth subcarbonate, allows the outer surface of the proximal shaft to be colored. In a preferred embodiment, less than 1% by weight of phthalocyanine blue and violet23 colorant are added to the outer tubular member 28.

Color can play an important role in the identification and use of selected catheters. For example, color can identify certain characteristics about the catheter that are not readily evident by looking at the catheter. For example, color can be used to distinguish between various diameter catheters. In addition, color bands or rings may be provided on the catheter shaft, at selected distances from the distal end of the catheter. These color bands or rings can be used to determine how far the distal end of the catheter is inserted into the body. These and other advantages are provided by coloring the outer surface of selected portions of the catheter. Thus, by axially disposing an outer layer that includes a non-metallic filler material around an inner layer that includes a highly radiopaque metallic filler material, the resulting catheter may be both highly radiopaque and have the advantages of a colored outer surface.

A number of methods are contemplated for manufacturing the multi-layer proximal shaft portion 12. A first illustrative method includes the steps of intermixing a first radiopaque filler material with a first plastic material, thereby providing a first extrudable material; intermixing a second radiopaque filler material with a second plastic material wherein the first radiopaque filler material is different from said second radiopaque filler material, thereby providing a second extrudable material; and co-extruding the first extrudable material and the second extrudable material to form the multi-layer tubular assembly. As discussed above, it is contemplated that the first plastic material may be the same or different from the second plastic material.

A second illustrative method comprises the steps of: intermixing a first radiopaque filler material with a first plastic material in a first concentration, thereby providing a first extrudable material; intermixing a second radiopaque filler material with a second plastic material in a second concentration, wherein the first concentration is different from the second concentration, thereby providing a second extrudable material; and co-extruding the first extrudable material and the second extrudable material to form the multi-layer tubular assembly. It is contemplated that the first radiopaque filler may the same or different from the second radiopaque filler material. Furthers it is contemplated that the first plastic material may be the same or different than the second plastic material.

A third illustrative method of the present invention comprises the steps of: intermixing a first radiopaque filler material with a first plastic material, thereby providing a first extrudable material; intermixing a second radiopaque filler material with a second plastic material wherein the first radiopaque filler material is different from said second radiopaque filler material, thereby providing a second extrudable material; extruding the first extrudable material; and extruding the second extrudable material in coaxial relation with the first extrudable material to form the multi-layer tubular assembly. As with the first illustrative method described above, it is contemplated that the first plastic material may be the same or different from the second plastic material.

Finally, a fourth illustrative method of the present invention comprises the step of: intermixing a first radiopaque filler material with a first plastic material in a first concentrations thereby providing a first extrudable material; intermixing a second radiopaque filler material with a second plastic material in a second concentration, wherein the first concentration is different from the second concentration, thereby providing a second extrudable material; extruding the first extrudable material; and extruding the second extrudable material in coaxial relation with the first extrudable material to form the multi-layer tubular assembly. As with the second illustrative method discussed above, it is contemplated that the first radiopaque filler may the same or different from the second radiopaque filler material. Further, it is contemplated that the first plastic material may be the same or different than the second plastic material.

FIG. 4 is an alternative cross section of the catheter of FIG. 1 taken along line 3—3 showing a braid 50. Braid 50 may be provided between inner tubular member 52 and outer tubular member 54, as shown. The construction and properties of inner tubular member 52 and outer tubular member 54 may be the same as described above with respect to inner tubular member 26 and outer tubular member 28.

Figure 5:
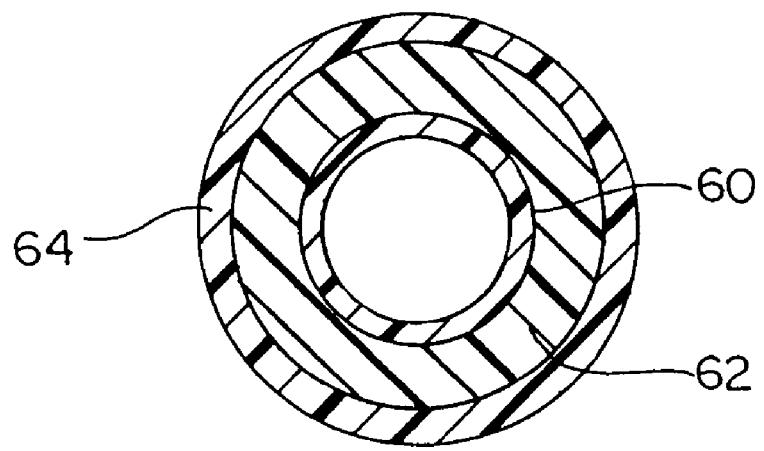
FIG. 5 is an alterative cross section of the catheter of FIG. 1 taken along line 3—3 showing a three layer proximal shaft section.

FIG. 5 is an alterative cross section of the catheter of FIG. 1 taken along line 3—3 showing a three layer proximal shaft section. In this embodiment, three layers are provided including an inner tubular member 60, an intermediate tubular member 62 and an outer tubular member 64. Preferably, the inner tubular member 60 and outer tubular member 64 have a radiopaque filler material that is selected to provide a relatively smooth surface. Further, the concentrations of the radiopaque filler material in the inner and outer tubular members is preferably less than the concentration of the radiopaque filler in the intermediate tubular member 62.

The intermediate tubular member 62 may have a radiopaque filler material that is selected to provide high radiopacity. Further, the concentration of the radiopaque filler material is preferably higher than that concentration of the radiopaque filler in the inner and outer tubular members 60 and 64. In this configurations the inner and outer tubular members 60 and 64 may provide relatively smooth inner and outer surfaces, while the intermediate layer 62 may provide high radiopacity.

In another illustrative embodiments the inner tubular member 60 may have a higher concentration of a radiopaque filler material than either the outer tubular member 64 or the intermediate tubular member 62. This illustrative embodiment recognizes that a smooth inner surface may not be required in selected applications such as angiographic applications. In these applications it may be more important to provide a highly radiopaque shaft portion.

Having thus described the preferred embodiments of the present invention, those of skill in the art will readily appreciate that yet other embodiments may be made and used within the scope of the claims hereto attached.

What is claimed:

1. A tubular assembly for an intravascular catheter comprising:
   a. a first tubular member having a proximal end, a distal end, and a lumen extending therethrough, said first tubular member comprising a first radiopaque filler material intermixed with a first plastic material; and
   b. a second tubular member in coaxial relation with and axially surrounding at least a portion of said first tubular member, said second tubular member comprising a second radiopaque filler material intermixed with a second plastic material, wherein said second radiopaque filler material is different from said first radiopaque filler material.

2. The tubular assembly of claim 1 wherein said first and second plastic materials are PEBA.

3. The tubular assembly of claim 1 wherein said first and second plastic materials are different materials.

4. The tubular assembly of claim 1 wherein said first radiopaque filler material is a metal based radiopaque filler.

5. The tubular assembly of claim 4 wherein said first radiopaque filler material is tungsten and said second radiopaque filler material is bismuth subcarbonate.

6. The tubular assembly of claim 5 wherein at least one of said first and second plastic materials contains a colorant.

7. A tubular assembly for an intravascular catheter comprising:
   a. a first tubular member having a proximal end, a distal end, and a lumen extending therethrough, said first tubular member comprising a first radiopaque filler material intermixed with a first plastic material, said first radiopaque filler material having a first concentration; and
   b. a second tubular member in coaxial relation with and axially surrounding at least a portion of said first tubular member, said second tubular member comprising a second radiopaque filler material intermixed with a second plastic material, said second radiopaque filler material having a second concentration wherein said first concentration is different from said second concentration.

8. The tubular assembly of claim 7 wherein said first and second plastic materials are PEBA.

9. The tubular assembly of claim 7 wherein said first and second plastic materials are different materials.

10. The tubular assembly of claim 7 wherein said first radiopaque filler material is a metal based radiopaque filler.

11. The tubular assembly of claim 8 wherein said first radiopaque filler material is tungsten and said second radiopaque filler material is bismuth subcarbonate.

12. The tubular assembly of claim 7 wherein the first radiopaque filler material and the second radiopaque filler material are the same filler material.

13. The tubular assembly of claim 7 wherein said first concentration is greater than said second concentration.

14. The tubular assembly of claim 7 wherein said first concentration is less than said second concentration.

15. The tubular assembly of claim 7 wherein at least one of said first and second plastic materials contains a colorant.

16. A tubular assembly for an intravascular catheter comprising:
   a. a first tubular member having a proximal end, a distal end, and a lumen extending therethrough, said first tubular member comprising a first radiopaque filler material intermixed with a first plastic material;
   b. a second tubular member having a proximal end, a distal end, said second tubular member in coaxial relation with and axially surrounding at least a portion of said first tubular member, said second tubular member comprising a second radiopaque filler material intermixed with a second plastic material, wherein said second radiopaque filler material is different from said first radiopaque filler material; and
   c. a distal tip attached to the distal end of at least one of said first and second tubular members, said distal tip comprising a third radiopaque filler material intermixed with a third plastic material.

17. The tubular assembly of claim 16 wherein said third radiopaque filler material is the same as the first radiopaque filler material.

18. The tubular assembly of claim 17 wherein said third radiopaque filler material and said first radiopaque filler material comprise tungsten.

19. The tubular assembly of claim 18 wherein said second radiopaque filler material comprises bismuth subcarbonate.

20. The tubular assembly of claim 19 wherein said third plastic material and the first plastic material are PEBA.

21. A tubular assembly for an intravascular catheter comprising:
   a. a first tubular member having a proximal end, a distal end, and a lumen extending therethrough, said first tubular member comprising a first radiopaque filler material intermixed with a first plastic material at a first concentration; and
   b. a second tubular member having a proximal end and a distal end, said second tubular member in coaxial relation with and axially surrounding at least a portion of said first tubular member and comprising a second radiopaque filler material intermixed with a second plastic material at a second concentration, wherein said first concentration is different from said second concentration; and
   c. a distal tip attached to the distal end of said first and second tubular members, said distal tip comprising a third radiopaque filler material intermixed with a third plastic material at a third concentration.

22. The tubular assembly of claim 21 wherein said first concentration is higher than said second concentration.

23. The tubular assembly of claim 22 wherein said first concentration is higher than said third concentration.

24. The tubular assembly of claim 22 wherein said first concentration is lower than said third concentration.

25. The tubular assembly of claim 21 wherein said first concentration is lower than said second concentration.

26. The tubular assembly of claim 25 wherein said first concentration is higher than said third concentration.

27. The tubular assembly of claim 25 wherein said first concentration is lower than said third concentration.

* * * * *